US009949637B1

(12) United States Patent
Wong et al.

(10) Patent No.: US 9,949,637 B1
(45) Date of Patent: Apr. 24, 2018

(54) FLUORESCENT IMAGING ON A HEAD-MOUNTABLE DEVICE

(71) Applicant: Verily Life Sciences LLC, Mountain View, CA (US)

(72) Inventors: Adrian Wong, Mountain View, CA (US); Philipp Helmut Schmaelzle, Los Altos, CA (US); Andrew Jason Conrad, Malibu, CA (US); Samuel D'Amico, Menlo Park, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 734 days.

(21) Appl. No.: 14/089,453

(22) Filed: Nov. 25, 2013

(51) Int. Cl.
*A61B 3/14* (2006.01)
*A61B 3/02* (2006.01)
*A61B 3/12* (2006.01)

(52) U.S. Cl.
CPC .............. *A61B 3/12* (2013.01); *A61B 3/1241* (2013.01)

(58) Field of Classification Search
CPC .......... A61B 3/113; A61B 2017/00345; A61B 5/04001; A61B 5/1114; A61B 5/14532; A61B 5/1455; A61B 5/6867; A61B 17/3403; A61B 2017/00057; A61B 2018/00642; A61B 2090/309; A61B 2090/373; A61B 5/0004; A61B 5/0006; A61B 5/0476; A61B 5/14507; G02B 2027/0132; G02B 2027/0138; G02B 2027/0187; G02B 2027/0198; G02B 27/0093; G02B 27/017; G02B 27/0172; G02B 5/30; G02B 2027/0136
(Continued)

(56) References Cited

U.S. PATENT DOCUMENTS 5,270,748 A  12/1993  Katz
5,621,572 A   4/1997  Fergason
(Continued)

FOREIGN PATENT DOCUMENTS

WO  2003/105679  12/2003
WO  2013/112554   8/2013

OTHER PUBLICATIONS

Fleming, Ioana N. et al., "Intraoperative Visualization of Anatomical Targets in Retinal Surgery," IEEE Workshop on Applications of Computer Vision, 2008, 6 pages.
(Continued)

*Primary Examiner* — Brandi Thomas
(74) *Attorney, Agent, or Firm* — McDonnell Boehnen Hulbert & Berghoff LLP

(57) ABSTRACT

Methods and apparatus are described herein for fluorescent imaging of a retina using a head-mountable device. The retina is illuminated by a head-mountable device (HMD) with light at an excitation wavelength of a fluorophore in the retina and imaged by the HMD at an emission wavelength of the fluorophore. The direction of gaze of a user of the HMD could be determined from the retinal image. The pattern of vasculature in the retinal image could be used to identify the user of the HMD. Information in the retinal image could be used to determine the medical state of the user and diagnose disease states. Fluorescent agents can be introduced into the vasculature of the wearer of the HMD to facilitate these or other applications of fluorescent imaging of the retina using the HMD.

11 Claims, 10 Drawing Sheets

(58) Field of Classification Search
 USPC ....... 351/200, 204, 205, 209, 208, 210, 211, 351/221, 222
 See application file for complete search history.

(56) References Cited

U.S. PATENT DOCUMENTS

| | | | |
|---|---|---|---|
| 5,982,555 A | 11/1999 | Melville et al. | |
| 6,394,602 B1 | 5/2002 | Morrison et al. | |
| 6,560,028 B2 | 5/2003 | Melville et al. | |
| 8,477,425 B2 | 7/2013 | Border et al. | |
| 2002/0006378 A1* | 1/2002 | Young | A61K 41/0076 424/1.11 |
| 2002/0049374 A1 | 4/2002 | Abreu | |
| 2004/0196399 A1 | 10/2004 | Stavely | |
| 2006/0200013 A1 | 9/2006 | Smith et al. | |
| 2007/0161786 A1* | 7/2007 | Mitsunaga | C09K 11/7777 534/15 |
| 2008/0088529 A1 | 4/2008 | Tang | |
| 2008/0273172 A1* | 11/2008 | Spaide | A61B 3/1233 351/206 |
| 2009/0234225 A1 | 9/2009 | Martin et al. | |
| 2010/0256597 A1* | 10/2010 | Prausnitz | A61F 9/0017 604/506 |
| 2010/0321409 A1 | 12/2010 | Komori et al. | |
| 2011/0248904 A1* | 10/2011 | Miyawaki | G02B 27/017 345/7 |
| 2011/0254698 A1 | 10/2011 | Eberl et al. | |
| 2012/0105310 A1 | 5/2012 | Sverdrup et al. | |
| 2013/0106674 A1 | 5/2013 | Wheeler et al. | |
| 2013/0265437 A1 | 10/2013 | Thorn et al. | |
| 2013/0300636 A1 | 11/2013 | Cunningham et al. | |
| 2014/0049451 A1 | 2/2014 | Sugiyama et al. | |
| 2014/0354514 A1* | 12/2014 | Aronsson | G06F 3/013 345/7 |

OTHER PUBLICATIONS

GMR Institute of Technology, "Wearing Computing—An Innovative Application of Neural Networks," www.PPTSworld.com, Sep. 1999, 10 pages.

Koronyo-Hamaoui et al., "Identification of Amyloid Plaques in Retinas from Alzheimer's Patients and Noninvasive In Vivo Optical Imaging of Retinal Plaques in a Mouse Model," Neuroimage, Jan. 2011, pp. S204-S217 (NIH Public Access Author Manuscript).

Lawson, Everett et al., "Computational Retinal Imaging via Binocular Coupling and Indirect Illumination," SIGGRAPH, Aug. 5-9, 2012, 1 page.

Neurovision Imaging, "NeuroVision Eye Test Part of Major Alzheimer's Trial," BusinessWire, Jun. 4, 2013, pp. 1-2.

\* cited by examiner

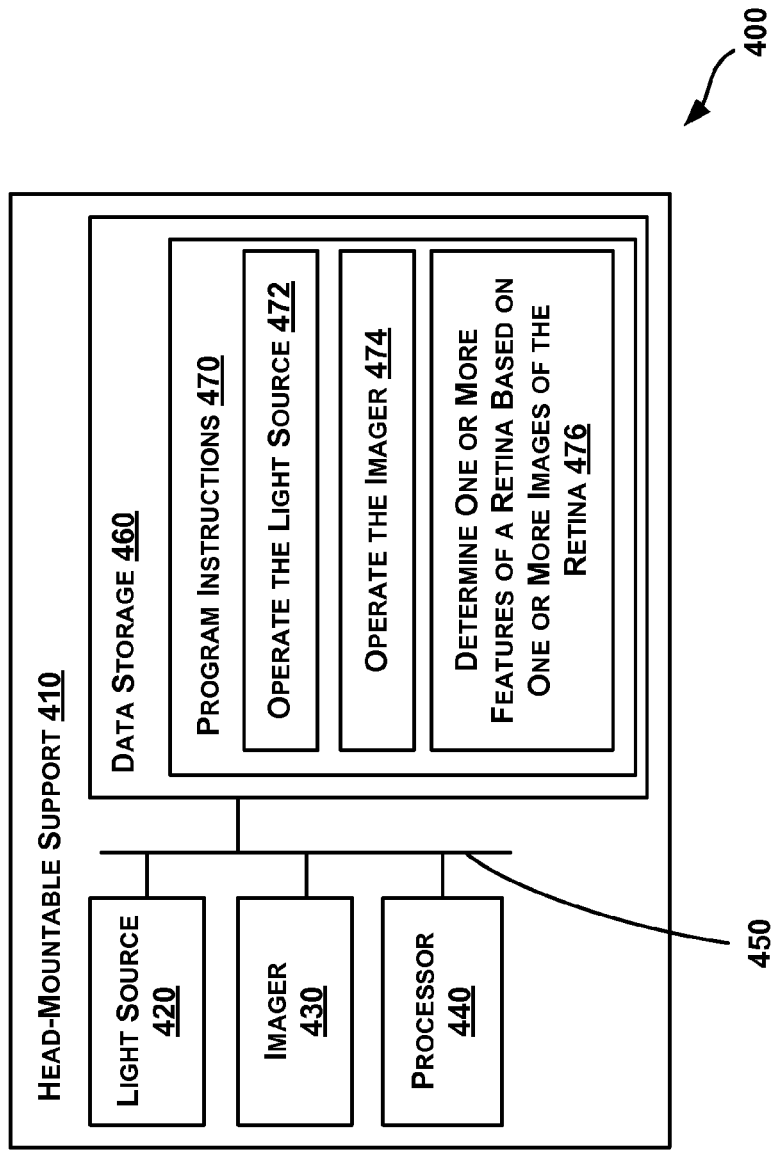

FLUORESCENT IMAGING ON A HEAD-MOUNTABLE DEVICE

BACKGROUND

Unless otherwise indicated herein, the materials described in this section are not prior art to the claims in this application and are not admitted to be prior art by inclusion in this section.

Wearable systems can integrate various elements, such as miniaturized computers, input devices, sensors, detectors, image displays, wireless communication devices as well as image and audio processors, into a device that can be worn by a user. Such devices provide a mobile and lightweight solution to communicating, computing and interacting with one's environment. With the advance of technologies associated with wearable systems and miniaturized optical elements, it has become possible to consider wearable compact optical displays that augment the wearer's experience of the real world.

By placing an image display element close to the wearer's eye(s), an artificial image can be made to overlay the wearer's view of the real world. Such image display elements are incorporated into systems also referred to as "near-eye displays", "head-mounted displays" or "heads-up displays" (HUDs). Depending upon the size of the display element and the distance to the wearer's eye, the artificial image may fill or nearly fill the wearer's field of view.

SUMMARY

Some embodiments of the present disclosure provide a method that involves: illuminating a retina in an eye with incident light from a light source in a head-mounted device, in which the incident light has a wavelength corresponding to an excitation wavelength of a fluorophore present in the retina; detecting, using a detector disposed in the head-mounted device, fluorescent light emitted from the fluorophore in response to the incident light; and determining a feature of the retina using the detected fluorescent light.

Some embodiments of the present disclosure provide a device that includes: a head-mountable support; a light source supported by the head-mountable support, in which the light source is configured to illuminate a retina in an eye with incident light that has a wavelength corresponding to an excitation wavelength of a fluorophore; and an imager supported by the head-mountable support, in which the imager is configured to image the retina using fluorescent light emitted from the fluorophore in response to the incident light.

Some embodiments of the present disclosure provide a system that includes: means for illuminating a retina in an eye with incident light that has a wavelength corresponding to an excitation wavelength of a fluorophore present in the retina; means for detecting fluorescent light emitted from the fluorophore in response to the incident light; and means for determining a feature of the retina using the detected fluorescent light.

BRIEF DESCRIPTION OF THE DRAWINGS

FIG. 4 is a functional block diagram of an HMD that is configured to image a retina of a wearer of the device, according to an example embodiment.

DETAILED DESCRIPTION

I. Overview

Figure 1:
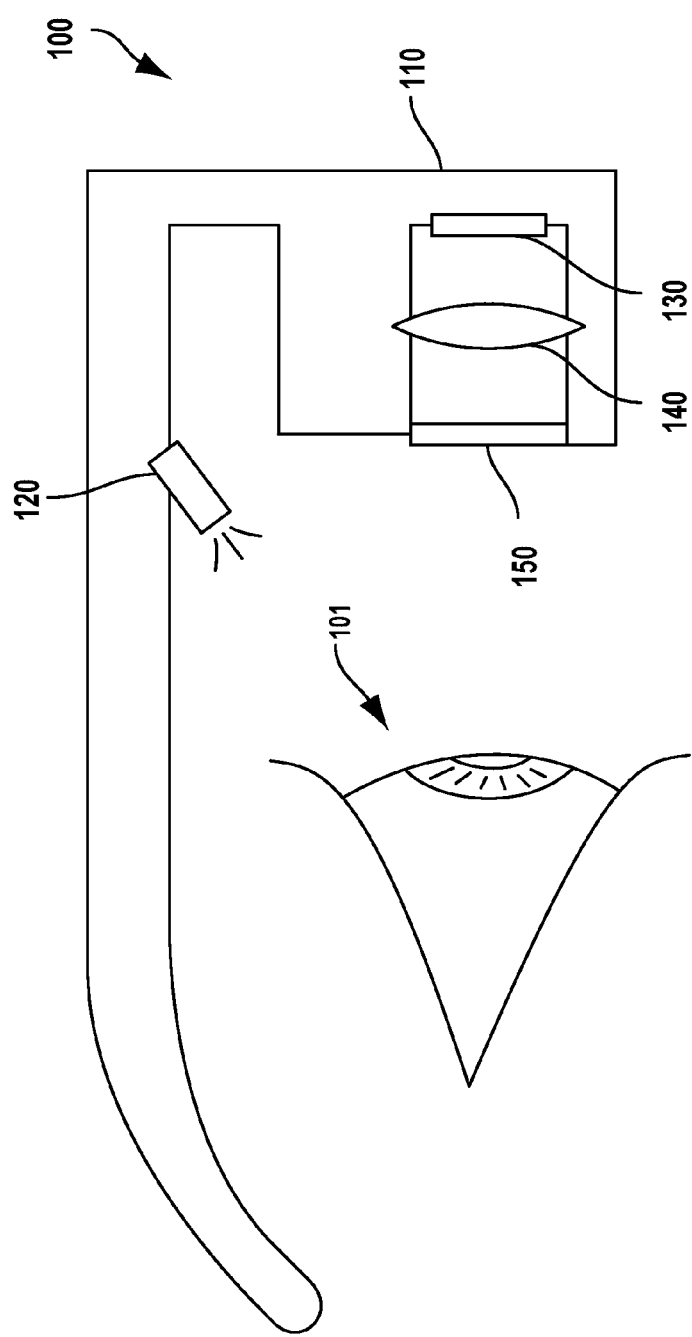
FIG. 1 illustrates a head-mountable device according to an example embodiment.

Disclosed herein are methods and systems for retinal imaging. In some examples, a head-mountable device (HMD) can include retinal imaging functionality. In this way, when the HMD is worn by a wearer, the HMD can image the retina of one or both of the wearer's eyes. The retinal imaging by HMD could occur automatically, or it could occur in response to an instruction from the wearer.

Including a retinal imaging system in an HMD could provide a number of useful functions to the HMD. The direction of gaze of a user of the HMD could be determined from the retinal image. This gaze direction information could be used to determine what the user was looking at, and this information could be used to alter the function of the HMD. The identity of the user of the HMD could be determined from the pattern of vasculature in the retinal image. This determination of identity could be used to alter the function of the HMD according to a personal configuration associated with the identified user. This identification could also be used as a form of biometric security, unlocking functions of the device for specific users or acting to identify the user to remote services accessed by the HMD. Information in the retinal image could also be used to determine the medical state of the user and diagnose disease states. For example, analysis of the vasculature of the retina could indicate that diabetic retinopathy was occurring; detection of this condition at an early stage could beneficially facilitate preventive treatment.

Obtaining images of the retina can be difficult because the reflection of external illumination from the retina can be much less bright than reflections of illumination from more superficial structures of the eye, such as the cornea. As a result, it can be difficult to isolate the low-level retinal image signal from the large-amplitude corneal reflection signal or other image signals. By imaging fluorescent light from a fluorophore in or on the retina, this difficulty could be overcome. The fluorophore could be illuminated at its excitation wavelength, and the retinal image could be taken using light of an emission wavelength of the fluorophore, which the fluorophore emits in response to the illumination. Because the emission wavelength is different than the excitation wavelength, an imaging sensor can be configured to detect the retinal image by being configured to be selectively sensitive to the emission wavelength and relatively insensitive to the wavelength of the illumination.

This fluorescent imaging of the retina could be implemented by imaging an existing fluorophore of the retina. For example, drusen in an optic disc of an eye of a wearer the HMD could be fluorescence-imaged according to methods or devices disclosed herein to determine gaze direction. Alternatively, a fluorophore could be introduced into the retina to enable fluorescent imaging. The fluorophore could be introduced into the retina by being introduced into the vasculature of the wearer of the HMD, for example through injection, transdermal application, ingestion, or some other method familiar to one skilled in the art. Alternatively, the fluorophore could be introduced through direct injection into the vitreous humor, the aqueous humor, or other aspects of the eye. The introduced fluorophore could selectively bind to targets which allow the retina to be imaged. The introduced fluorophore could be a fluorescent nanoparticle functionalized with a target-specific binding moiety. Alternatively, the nanoparticle could selectively bind to a target, and the nanoparticle could be functionalized with a fluorophore.

The fluorophore could be part of or could selectively bind to medically-relevant analytes, allowing fluorescent retinal imaging from an HMD to enable diagnosis of a medical condition associated with the presence of the medically-relevant analyte. For example, the nanoparticle could be curcumin and could selectively bind to a beta-amyloid peptide associated with Alzheimer's disease. Other targets and/or nanoparticles could be used. For example, a target-specific antibody could be used. The target-specific antibody could be functionalized with a fluorescent moiety to enable fluorescent imaging of the target-specific antibody and/or any target it may complex with.

In some implementations, the fluorophore can be present at discrete locations in the retina, such as by aggregating into a sufficiently small number of discrete fluorescent aggregates. The fluorescent imaging of the retina may then show a "constellation" of discrete fluorophore or discrete fluorophore aggregate locations in the retina. Further, if the fluorophore is present in blood circulating in the vasculature of the retina, imaging this constellation over time could allow for the detection of a heart rate, a blood flow rate and/or flow profile in the vasculature, eye saccades, or other features of the retina of the wearer of the HMD.

A fluorescent imaging system of an HMD could be incorporated into a display element of the HMD. The display element could include optics which could allow patterned light from a display panel to be projected in-focus on the surface of a retina of the wearer of the HMD. For example, the wearer of the HMD may position the HMD such that the display is substantially located on a focal plane that is conjugate with a focal plane at the wearer's retina. The optical system could then provide a second focal plane that is conjugate with the focal plane of the wearer's retina. An imaging sensor of the fluorescent imaging system could be located at the second focal plane. Thus, the wearer's efforts to position the HMD such that the patterned light from the display panel is in-focus on the wearer's retina could also serve to position the HMD such that emitted fluorescent light form the retina is in-focus on the imaging sensor of the fluorescent imaging system.

II. Example Head-Mountable Devices

Systems and devices in which example embodiments can be implemented will now be described in greater detail. In general, an example system can be implemented in or can take the form of a head-mountable device (HMD). An HMD can generally be any device that is capable of being worn on the head and places an imaging device in front of one or both eyes of the wearer. An HMD can take various forms such as a helmet or eyeglasses. As such, references to "eyeglasses" or a "glasses-style" HMD should be understood to refer to an HMD that has a glasses-like frame so that it can be worn on the head. Further, example embodiments can be implemented by or in association with an HMD operating to image one or both eyes, which can be referred to as a "monocular" HMD or a "binocular" HMD, respectively.

FIG. 1 illustrates elements of an HMD according to an example embodiment, which takes the form of a monocular HMD 100. Elements of HMD 100 and an eye 101 of a wearer of the HMD 100 are shown in FIG. 1. HMD 100 can include a head-mountable support 110, a light source 120, an imaging sensor 130, an imaging optical system 140, and a light filter 150. Head-mountable support 110 is configured to support other elements of the HMD 100 (e.g., 120, 130, 140, 150) and to be mounted onto a head of the wearer of the HMD 100 such that a retina of the eye of the wearer 101 can be fluorescently imaged.

The light source 120 can be configured to produce light of a wavelength corresponding to an excitation wavelength of a fluorophore. The light source 120 can be supported by the head-mountable support 110 such that when a person wears HMD 100 the light source 120 is able to illuminate the retina of the wearer's eye 101 and excite fluorophores in the retina that have an excitation wavelength corresponding to the wavelength of the light produced by the light source 120. The excitation wavelength could be, for example, in the visible, ultra-violet, or infrared portions of the electromagnetic spectrum. The light source 120 can be located on HMD 100 as illustrated in FIG. 1 or another location on HMD 100 such that the light source 120 is able to illuminate the retina of the eye of the wearer 101. The location of the light source on HMD 100 could be chosen to minimize the amount of illumination light that interferes with imaging of the retina. For example, the retina could be illuminated off-axis, as show in FIG. 1 (off-axis referring to the illumination being projected along an axis that is sufficient different from, or 'off,' the axis of components 130, 140, 150 that are used to image the retina. To further minimize the interference of imaging by illumination light, the retina could be illuminated through a temple of the wearer of HMD 100. That is, HMD 100 could be configured such that the light source 120 is localized proximate the temple of the wearer and oriented such that the light emitted by the light source 120 can be transmitted through the temple of the wearer to illuminate the retina of the eye of the wearer 101.

The image sensor 130 can include a photodetector array that is sensitive to light of a wavelength corresponding to an emission wavelength that is emitted by the fluorophore in response to the illumination at the excitation wavelength from the light source 120. For example, the image sensor 130 could include an array of CMOS active pixel elements. In another example, the image sensor 130 could include a CCD image sensor array. Other types of image sensor 130 are possible as well. The image sensor 130 can be supported by the head-mounted support 110 such that light emitted or reflected from the retina of the wearer's eye 101 is imaged by the image sensor 130.

The imaging optical system 140 includes optical elements configured to couple the image sensor 130 to the retina of the eye of the wearer 101 such that the retina is at a focal plane that is conjugate to a focal plane at the image sensor 130. For example, imaging optical system 140 could include one or more lenses and/or mirrors supported by the head-mountable support 110 and configured to focus light emitted from the fluorophore present in the retina such that the retina can be imaged in-focus by the image sensor 130. The imaging optical system 140 could also be configured to accept the light from the light source 120 and direct the light from the light source 120 to the retina of the wearer's eye 101.

The light filter 150 could include one or more wavelength-selective filters, reflectors, or other elements configured to preferentially allow light with wavelengths at or near the emission wavelength to reach the image sensor 130 and/or preferentially prevent light with wavelengths at or near the excitation wavelength (i.e., the light produced by the light source 120) to reach the image sensor 130. For example, the light filter 150 could include a dichroic filter that selectively passes light of wavelengths corresponding to the emission wavelength of the fluorophore. The light filter 150 could be supported by the head-mountable support 110 and located as shown in FIG. 1 or it could be located at other locations in the path taken by light emitted from the retina to the image sensor 130. For example, the light filter could be located between the optical system 140 and the image sensor 130; further, the light filter 150 could be integrated into the image sensor 130. Additionally or alternatively, the light filter 150 could be incorporated into the optical system 140.

Figure 2:
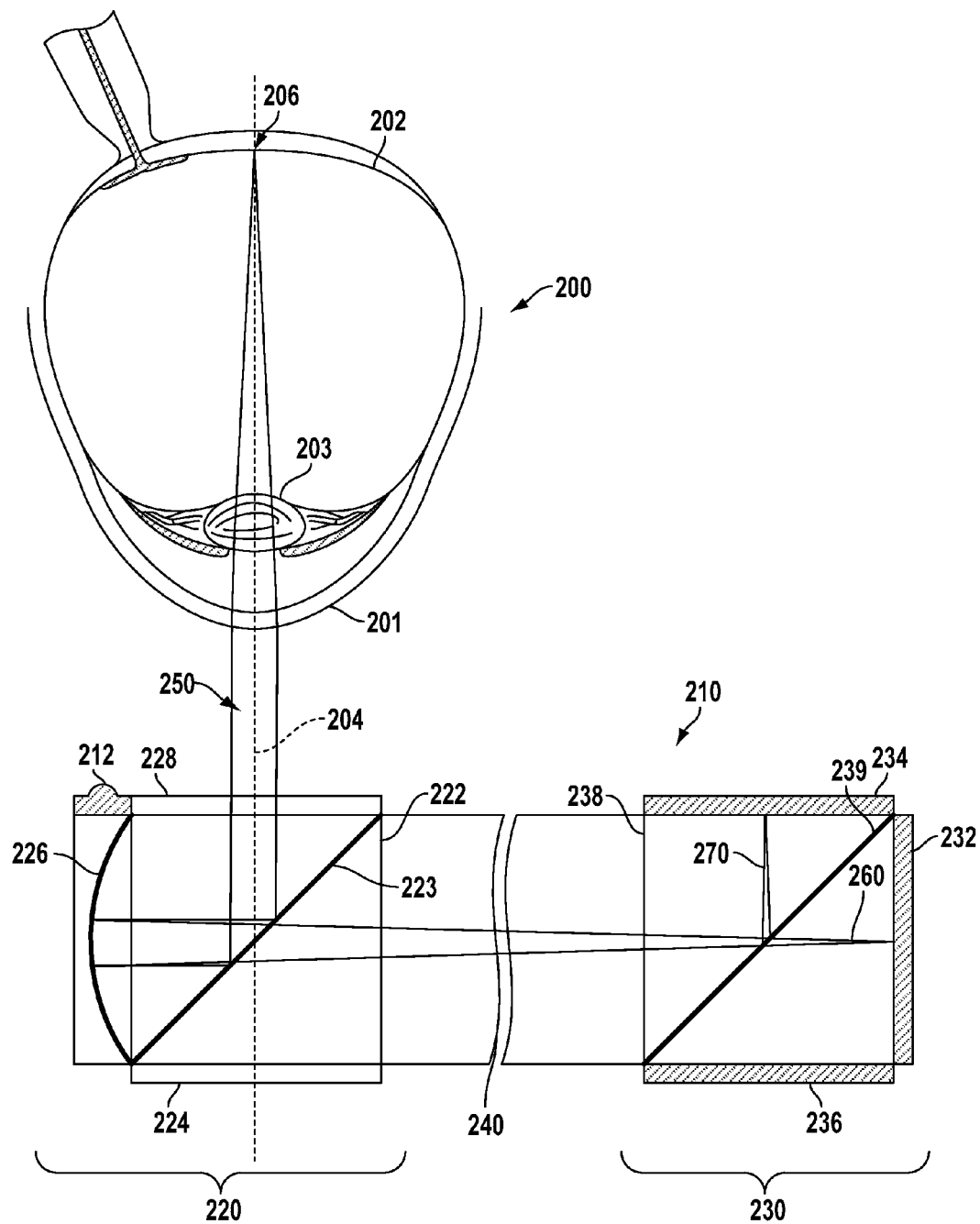
FIG. 2 illustrates another head-mountable device according to an example embodiment.

FIG. 2 illustrates a cross-sectional view of elements of a monocular HMD according to an example embodiment. The HMD includes optical system 210 that is supported by a head-mountable support (not shown). The head-mountable support can be configured to allow for stable mounting of the HMD on a head of a wearer. The head-mountable support can configured to support the HMD on one or more of an ear, a nose, or another aspect of the head of the wearer. Also shown in FIG. 2 is an eye 200 of the wearer, as well as a cornea 201, retina 202, and crystalline lens 203 in the eye 200. The cross-sectional view of FIG. 2 is taken horizontally through the eye 200 of the wearer and through the optical system 210 of the HMD worn by the wearer. That is, movement out of the page of FIG. 2 corresponds to upward vertical movement relative to the wearer (toward the top of the head of the wearer) and movement into the page of FIG. 2 corresponds to downward vertical movement relative to the wearer (toward a foot of the wearer).

In this example, a fluorophore is present in the retina 202. The fluorophore may be naturally present in the retina 202 or may be introduced into the retina 202 by intravenous injection, oral administration, or some other method. The structure of the eye 200 and the retina 202 define a gaze direction 204 that represents the direction the wearer is looking. The retina 202 includes an example point on the retina 206 that is located at the intersection of the gaze direction 204 and the retina 202. The location and scale of the optical system 210 of the HMD as shown in FIG. 2 in relation to the eye 200 and the gaze direction 204 are not meant to be limiting, but to act as an illustration of the components and operation of an example embodiment.

The optical system 210 can include a light source 212. The light source 212 can be configured to produce light of a wavelength corresponding to an excitation wavelength of the fluorophore in the retina 202. The light source 212 can be located in the optical system 210 such that when a user wears the HMD the light source 212 is able to illuminate the retina 202 and excite the fluorophore that has an excitation wavelength corresponding to the wavelength of the light produced by the light source 212. The light source 212 can be located in the optical system 210 as illustrated in FIG. 2 or located at another location on the HMD such that the light source 212 is able to illuminate the retina 202. The location of the light source on the HMD could be chosen to minimize the amount of illumination light that interferes with imaging of the retina 202. For example, the retina could be illuminated off-axis (off-axis referring to the illumination being projected along an axis that is sufficient different from, or 'off,' the axis of the light and components that could be used to image the retina 202). For example, the light source 212 can be located in the HMD such that when a user wears the HMD the light source 212 is able to illuminate the retina 202 through a temple of the wearer.

For purposes of illustration, the optical system 210 can be described in terms of a proximal portion 220 and a distal portion 230. In typical operation, the proximal portion 220 is proximal to the eye 200 of the wearer, whereas the distal portion 230 is located some distance away from the eye 200 of the wearer. In the example illustrated in FIG. 2, the optical system 210 extends horizontally such that distal portion 230 is to the left of the proximal portion 220 from the perspective of the wearer. It is to be understood, however, that other configurations are possible. For example, the distal portion 230 could be to the right of the proximal portion 220, or optical system 210 could extend vertically, with distal portion 230 located above or below proximal portion 220. Other configurations are also possible.

The optical system 210 may be able to generate a virtual image that is viewable, by the wearer using eye 200, when the gaze direction 204 is substantially aligned with the proximal portion 220 as shown in FIG. 2. The wearer may also be able to view the wearer's real-world environment along the gaze direction 204. In an example embodiment, the real-world environment and the virtual image are viewable simultaneously. For example, the virtual image might overlay a portion of the observer's view of the real-world environment. The virtual image could appear to the wearer to be located at or near infinity. Alternatively, the virtual image could appear to be located within the immediate surroundings of the wearer. For example, the apparent distance of the virtual image could be in the range of about 0.5 to 4 meters.

In an example embodiment, the gaze direction 204 passes through a proximal beam splitter 222. The eye 200 of the wearer may be located on one side of proximal beam splitter 222, and the other side of the proximal beam splitter 222 may be provided with a viewing window 224 that allows light into the proximal beam splitter 222 from outside of the optical system 210. In this way, the wearer is able to view the real world through the viewing window 224 and the proximal beam splitter 222, along the gaze direction 204.

The proximal beam splitter 222 includes a proximal beam-splitting interface 223 that is configured to combine light entering the proximal beam splitter 222 through the viewing window 224 with light from the virtual image generated by the optical system 210, so that both the real-world environment and the virtual image can be viewed along the gaze direction 204. For example, the proximal beam-splitting interface 223 may be in a plane that intersects the gaze direction 204 at an angle, such as a 45-degree angle.

In an example embodiment, the proximal beam-splitting interface 223 is configured to transmit the light entering through the viewing window 224 so that it is viewable along the gaze direction 204 and to reflect the light corresponding to the virtual image so that it is also viewable along the gaze direction 204. Further, the proximal beam-splitting interface 223 can be configured to reflect light emitted or reflected from the retina 202 so that the retina 202 can be imaged by the optical system 210. In this regard, the proximal beam splitter 223 may be optically coupled to an image former 226, which may be located in the proximal portion 220 as shown in FIG. 2. The image former 226 may include a concave mirror that reflects light corresponding to the virtual image and light corresponding to the image of the retina 202. Thus, the light from outside entering through the viewing window 224 may propagate along the gaze direction 204 so that it is transmitted through the beam-splitting interface 223 toward the retina 202 of the wearer, and the light corresponding to the virtual image may propagate in the left direction from the image former 216 until it is reflected towards the retina 202 by the beam-splitting interface 223. Further, the light emitted or reflected from the retina 202 may propagate from the retina 202 until it is reflected toward the image former 226 by the beam splitting interface 223.

In the example illustrated in FIG. 2, the proximal beam splitter 222 is a 45-degree beam splitter. Thus, the proximal beam-splitting interface 223 is in a plane that forms 45-degree angles with the faces of the beam splitter 222. As a result, the proximal beam-splitting interface 223 intersects the example gaze direction 204 at 45 degrees. It is to be understood, however, that other angles are possible.

In an example embodiment, the proximal beam splitter 222 is a 50/50 beam splitter, in which the beam-splitting interface 223 reflects half of any incident light and transmits the other half of the incident light. In order to prevent stray light in the optical system 210 from interfering with imaging the retina 202, the viewing window 224 may include a light filter that selectively blocks light of wavelengths corresponding to the emission wavelength of the fluorophore. Further, the optical system 210 may include an inner window 228 that includes a light filter that selectively blocks light of wavelengths corresponding to the wavelength of the light produced by the light source 212.

The optical system 210 includes an imager 232 that is configured to image the retina 202 using light emitted from the fluorophore in the retina 202 in response to illumination of the retina 202 by light produced by the light source 212. The imager 232 can include a photodetector array that is sensitive to light of a wavelength corresponding to the emission wavelength of the fluorophore. For example, the imager 232 could include an array of CMOS active pixel elements. In another example, the imager 232 could include a CCD image sensor array. The imager 232 could also include a light filter that selectively blocks light of wavelengths other than the emission wavelength of the fluorophore from being imaged by the imager 232. Additionally or alternatively, the imager 232 could include a light filter which selectively blocks light of wavelengths corresponding to the wavelength of the light produced by the light source 212 to illuminate the fluorophore in the retina 202. The imager 232 may be configured to capture still images and/or video.

The optical system 210 can include a display panel 234 that is configured to generate a light pattern from which the virtual image is formed. The display panel 234 may be an emissive display such as an Organic Light Emitting Diode (OLED) display. Alternatively, the display panel 234 may be a light modulator, such as a liquid-crystal on silicon (LCoS) array or a micro-mirror display such as a digital light processor (DLP), so as to generate the light pattern by spatially modulating light from a display light source 236. The display light source 236 may include, for example, one or more light-emitting diodes (LEDs) and/or laser diodes. The light pattern generated by the display panel 234 could be monochromatic, or it could include multiple colors (such as red, green, and blue) to provide a color gamut for the virtual image.

As shown in FIG. 2, the imager 232, the display panel 234, and the display light source 236 may be located in the distal portion 230 and optically coupled to a distal beam splitter 238. The distal beam splitter 238 is, in turn, optically coupled to the proximal beam splitter 222, for example, via a light pipe 240. In an example embodiment, the distal beam splitter 238 includes a distal beam-splitting interface 239.

In the example shown in FIG. 2, the distal beam-splitting interface 239 is in a plane parallel to the plane of the proximal beam-splitting interface 223. It is to be understood that the configuration of the proximal beam splitter interface 223 and the distal beam splitter interface 239 to be in parallel planes is exemplary only; the beam splitter interfaces 223, 239 could occupy perpendicular planes or planes with any other relationship. Further, the 45-degree angle formed by the distal beam-splitting interface 239 is exemplary only. Other angles could be used.

With the display panel 234 located on the face of the distal beam splitter 238 toward the wearer, the display light source 236 may be located on the opposite face of the distal beam splitter 238. With this configuration, light from the display light source 236 could reach the display panel 234. In particular, the distal beam-splitting interface 239 could transmit at least a portion of the light from the display light source 236 so that it could reach the display panel 234. Additionally, the distal beam-splitting interface 239 could reflect at least a portion of the light from the display light source 236 to the imager 232. The display panel 234 could spatially modulate the incident light, and the distal beam-splitting interface 239 could reflect at least a portion of the spatially-modulated light from the display panel 234 toward the proximal beam splitter 222. The proximal beam-splitting interface 223 could transmit at least a portion of the spatially-modulated light so that it reaches the image former 226. The image former 226 could then form a virtual image from the spatially-modulated light, and the proximal beam-splitting interface 223 could reflect at least a portion of the spatially modulated light from the image former 226 so that the virtual image is viewable along the gaze direction 204.

This configuration could also allow light emitted or reflected by the retina 202 to be imaged by the imager 232. In particular, light emitted or reflected from the retina 202 could propagate toward the proximal beam splitter 222 along the gaze direction 204. The proximal beam-splitting interface 223 could reflect at least a portion of the incident image light toward the image former 226. The image former 226 could then reflect the image light toward the imager 232. The image light could be at least partially transmitted by each of the proximal beam-splitting interface 223 and the distal beam-splitting interface 239 on its way from the image former 226 to the imager 232.

In an example embodiment, the distal beam splitter 238 is a polarizing beam splitter, in which the distal beam-splitting interface 239 preferentially reflects s-polarized light and preferentially transmits p-polarized light. In that case, the display light source 236 may include a linear polarizer that selectively transmits p-polarized light. The p-polarized light from the display light source 236 is preferentially transmitted by the distal beam-splitting interface 239 so that it is incident on the display panel 234. In this example, the display panel 234 is a liquid crystal on silicon (LCOS) display panel. As such, the display panel 234 spatially modulates the incident p-polarized light and also changes its polarization. Thus, in this example, the display panel 234 converts the incident p-polarized light into a spatially-modulated light pattern of s-polarized light. The distal beam-splitting interface 239 reflects the s-polarized spatially-modulated light from the display panel 234 toward the proximal portion 220. The proximal portion 220 can then modify the s-polarized spatially-modulated light as described above so that a virtual image is viewable along the gaze direction 204.

Depending on the emission and excitation wavelengths of the fluorophore, an HMD could use the display light source 236 to illuminate the retina 202. For example, during a first time period, the display light source 236 could illuminate the display panel 234 and the display panel 234 could spatially modulate the incident light from the display light source 236 to produce a virtual image from which the cornea 201 and crystalline lens 203 in the eye 200 form a real image on the retina 202. During a second time period, the display light source 236 could illuminate the display panel 234 and the display panel 234 could spatially modulate the incident light from the display light source 236 such that an area of the retina 202 is uniformly illuminated. This uniform illumination could be at a wavelength corresponding to the excitation wavelength of the fluorophore. The fluorophore could emit fluorescent light at an emission wavelength of the fluorophore in response to the uniform illumination, and the imager 232 could image the retina 202 using the fluorescent light during the second time period. In another example, the display panel 234 could spatially modulate the incident light from the display light source 236 during a plurality of time periods such that a different specified subsection of the retina 202 was illuminated during each of the time periods in the plurality of time periods, such that the image sensor could build a complete fluorescent image of the retina 202 using light detected during each of the time periods in the plurality of time periods.

Although an example is described above in which the proximal beam splitter 222 is a 50/50 beam splitter and the distal beam splitter 238 is a polarizing beam splitter, it is to be understood that the proximal beam splitter 222 and/or the distal beam splitter 238 could be differently configured. For example, one or both of the beam splitters 222, 238 could be a non-polarizing 80-20 beam splitter, in which the beam-splitting interface 223, 239 could transmit 80% of the incident light and reflect 20% of the incident light independent (or largely independent) of polarization. In the case where the proximal beam splitter 222 is configured this way, about 80% of the light entering through the viewing window 224 may reach the retina 202 of the wearer through the proximal beam-splitting interface 223 (instead of only about 50% when proximal beam splitter 222 is a 50/50 beam splitter). On the other hand, the proximal beam-splitting interface 223 would reflect only about 20% of the light from the image former 226 to the retina 202 or from the retina 202 to the imager 232. To compensate for the reduced reflectivity, the brightness of the light source 212 and/or the display light source 236 could be increased.

In an example embodiment, the proximal beam splitter 222, the distal beam splitter 238 and the light pipe 240 are made of glass. However, in order to reduce the weight of the optical system 210, some or all of these elements could be made of plastic instead of glass. A suitable plastic material is Zeonex® E48R cyclo olefin optical grade polymer, which is available from Zeon Chemicals L.P., Louisville, Ky. Another suitable plastic material is polymethyl methacrylate (PMMA).

With the configuration of optical system 210 described above, image former 226 can focus light from the display panel 234 onto the retina 202, via the optical elements in the wearer's eye 200 (including cornea 201 and crystalline lens 203) and can also focus light emitted from the retina 202 through the optical elements in the wearer's eye 200 (including cornea 201 and crystalline lens 203) onto the imager 232. That is, the optical system 210 can be configured to optically couple the display panel 234 and the imager 232 to the retina 202 in the wearer's eye 200 such that the retina 202 is at a focal surface that is conjugate to both a focal surface at the display panel 234 and another focal surface at the imager 232. As a result, when the wearer has adjusted the optical system 210 such that the virtual image viewed by the wearer's eye 200 appears to be in focus, light emitted from the retina 202 in the wearer's eye 202 is in focus on the imager 232.

To illustrate this arrangement, FIG. 2 includes an example common optical path 250. The common optical path 250, along with an example image sensor optical path 260, illustrates the path of light emitted or reflected from the example point on the retina 206 as it travels through the eye 200, to the optical system 210, and through the optical system 210 to be detected at a point on the imager 232. Conversely, example common optical path 250, along with an example display optical path 270, illustrates the path of light emitted from a point on the display panel 234 as it travels through the optical system 210, to the eye 200, and through the eye 200 to the example point on the retina 206.

The example image sensor optical path 260 and the example display optical path 270 are mirror images of each other about the plane of the distal beam-splitting interface 239. As a result, if the wearer adjusts one or more of the direction of gaze of the eye 200, the focus of the eye 202, and the location of the optical system 210 relative to the eye 200 such that virtual image light produced by the display panel 234 is in-focus at the example point on the retina 206, then light emitted or reflected from the example point on the retina 206 can be imaged in-focus at the imager 232.

It should be noted that the gaze direction 204, the point on the retina 206, the common optical path 250, the image sensor optical path 260, and the display optical path 270 are only illustrative examples used to describe the optical system 210 being configured to optically couple the display panel 234 and the imager 232 to the retina 202 of the wearer such that the retina 202 is at a focal surface that is conjugate to both a focal surface at the display panel 234 and another focal surface at the imager 232. Image former 226 can be configured so that a plurality of points on the retina 202 (including the example point on the retina 206) can be imaged in-focus at the imager 232. This same portion of the retina 202 can also receive the light from the display panel 234 when the image former 226 is used to produce a virtual image that is focused onto the retina 202 by the optical elements within the wearer's eye 200 (including the cornea 201 and crystalline lens 203).

Further, optical system 210 is only one example of an optical system which could be configured to optically couple a display and a fluorescent imager to a retina of a wearer such that the retina is at a focal surface that is conjugate to both a focal surface at the display and another focal surface at the fluorescent imager.

Figure 3A:
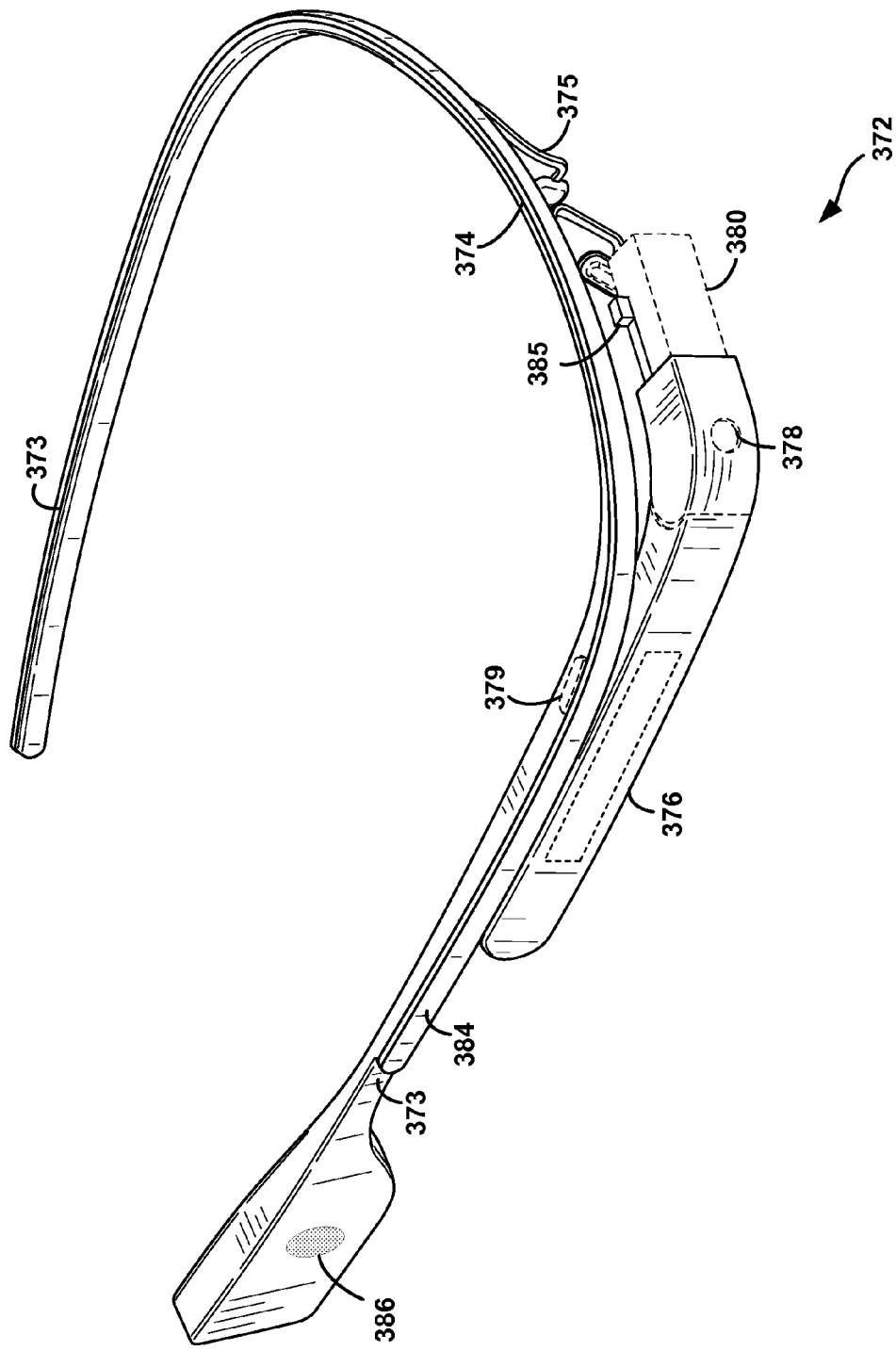
FIG. 3A illustrates another head-mountable device according to an example embodiment.

FIG. 3A illustrates a head-mountable device (HMD) according to an example embodiment, which takes the form of a monocular HMD 372. HMD 372 can include side-arms 373, a center frame support 374, and a bridge portion with nosepiece 375. In the example shown in FIG. 3A, the center frame support 374 connects the side-arms 373. HMD 372 does not include lens-frames containing lens elements; however, other embodiments could include lens-frames and lens elements. WCD 372 can additionally include a component housing 376, which can include an on-board computing system (not shown), an image capture device 378, and a button 379 for operating the image capture device 378 (and/or usable for other purposes). Component housing 376 can also include other electrical components and/or can be electrically connected to electrical components at other locations within or on the HMD.

HMD 372 also includes a speaker 386 for generating audio output. In one example, the speaker could be in the form of a bone conduction speaker, also referred to as a bone conduction transducer (BCT). Speaker 386 can be, for example, a vibration transducer or an electroacoustic transducer that produces sound in response to an electrical audio signal input. The frame of HMD 372 can be designed such that when a user wears HMD 372, the speaker 386 contacts the wearer. Alternatively, speaker 386 can be embedded within the frame of HMD 372 and positioned such that, when HMD 372 is worn, speaker 386 vibrates a portion of the frame that contacts the wearer. In either case, HMD 372 can be configured to send an audio signal to speaker 386, so that vibration of the speaker can be directly or indirectly transferred to the bone structure of the wearer. When the vibrations travel through the bone structure to the bones in the middle ear of the wearer, the wearer can interpret the vibrations provided by BCT 386 as sounds.

Various types of bone-conduction transducers (BCTs) can be implemented, depending upon the particular implementation. Generally, any component that is arranged to vibrate HMD 372 can be incorporated as a vibration transducer. Yet further it should be understood that HMD 372 can include a single speaker 386 or multiple speakers. In addition, the location(s) of speaker(s) on the WCD can vary, depending upon the implementation. For example, a speaker can be located proximate to a wearer's temple (as shown), behind the wearer's ear, proximate to the wearer's nose, and/or at any other location where the speaker 386 can vibrate the wearer's bone structure.

HMD 372 can include an optical system 380, which can be coupled to one of the side-arms 373 via the component housing 376. In an example embodiment, the optical system 380 can be made of glass and/or another transparent or translucent material, such that the wearer can see their environment through the optical system 380. Further, the component housing 376 can include a display and an imager (not shown) optically coupled to the optical system 380 and/or optical elements (not shown) to direct light between the display and the imager and the exposed aspects of the optical system 380. As such, optical system 380 can include further optical elements that direct light that is generated by the display towards the wearer's eye and that direct light emitted or reflected by the wearer's eye towards the imager when HMD 372 is being worn.

Optical features of the optical system 380 can be further configured such that, when the wearer has adjusted the direction and focus of their eye such that the light generated by the display is in-focus on the wearer's retina, light emitted or reflected by the retina is in-focus on the imager. That is, the optical system 380 can be configured to optically couple the display and the imager to the retina of the wearer of the HMD 372 such that the retina is at a focal surface that is conjugate to both a focal surface at the display and another focal surface at the imager. The disposition and configuration of the optical elements of the optical system 380 can be similar to the configuration of the proximal portion 230, the distal portion 230, and the light pipe 240 of the optical system 210 described in FIG. 2, or can be configured in another way.

HMD 372 can also include a light source 385. The light source 385 can be configured to produce light of a wavelength corresponding to an excitation wavelength of a fluorophore. The light source 385 can be located on or near the optical system 380 such that when a user wears HMD 372 the light source 385 is able to illuminate the retina of the wearer and excite fluorophores in the retina that have an excitation wavelength corresponding to the wavelength of the light produced by the light source 385. The light source 385 can be located on HMD 372 as illustrated in FIG. 3A or located at another location on HMD 372 such that the light source 385 is able to illuminate the retina of the wearer of the HMD 372. The light source 385 could be configured to project light into the optical system 380 and the optical system 380 could be configured to direct the light produced by the light source 385 toward the eye of the wearer of the HMD 372. The light source 385 can be located on HMD 372 such that the location of the light source 385 minimizes the amount of illumination light that interferes with imaging of the retina of the wearer. For example, the retina could be illuminated off-axis (off-axis referring to the illumination being projected along an axis that is sufficient different from, or 'off,' the axis of the light and components that could be used to image the retina of the wearer). For example, the light source 385 can be located on the HMD 372 such that when a user wears the HMD 372 the light source 385 is able to illuminate the retina of the wearer through a temple of the wearer.

The imager can include an array of photodetectors. For example, the imager could include an array of CMOS active pixel elements. In another example, the imager could include a CCD image sensor array. The imager can be configured to be sensitive to light of a wavelength corresponding to an emission wavelength of a fluorophore. For example, the imager could include a filter that selectively passes light of wavelengths corresponding to the emission wavelength. Alternatively, the optical system 380 could include a wavelength-selective filter, reflector, or other element configured to allow only light of wavelengths corresponding to the emission wavelength to reach the imager. The imager could alternatively or additionally be configured to be insensitive to light of a wavelength corresponding to the wavelength of the light emitted by the light source 385. Alternatively, the optical system 380 could include a wavelength-selective filter, reflector, or other element configured to prevent light of wavelengths corresponding to the wavelength of the light emitted by the light source 385 to reach the imager.

The display can be a system that generates a spatially-modulated pattern of light. For example, the display could include an organic light-emitting diode (OLED) array. In other examples, the display could include an array of selectively reflective or transmissive elements and a display light source. For example, the display could include a liquid crystal on silicon (LCoS) display panel or an array of digital micromirrors. The HMD 372 could further include a display light source (not shown) that could generate display light that the array of selectively reflective or transmissive elements could spatially modulate to generate the spatially modulated pattern of light. The optical system 380 could be configured to facilitate such a relationship between the display light source and array of selectively reflective or transmissive elements.

In a further aspect, HMD 372 can include a sliding feature 384, which can be used to adjust the length of the side-arms 373. Thus, sliding feature 384 can be used to adjust the fit of HMD 372. Further, HMD 372 can include other features that allow a wearer to adjust the fit of the HMD, without departing from the scope of the invention.

Figure 3B:
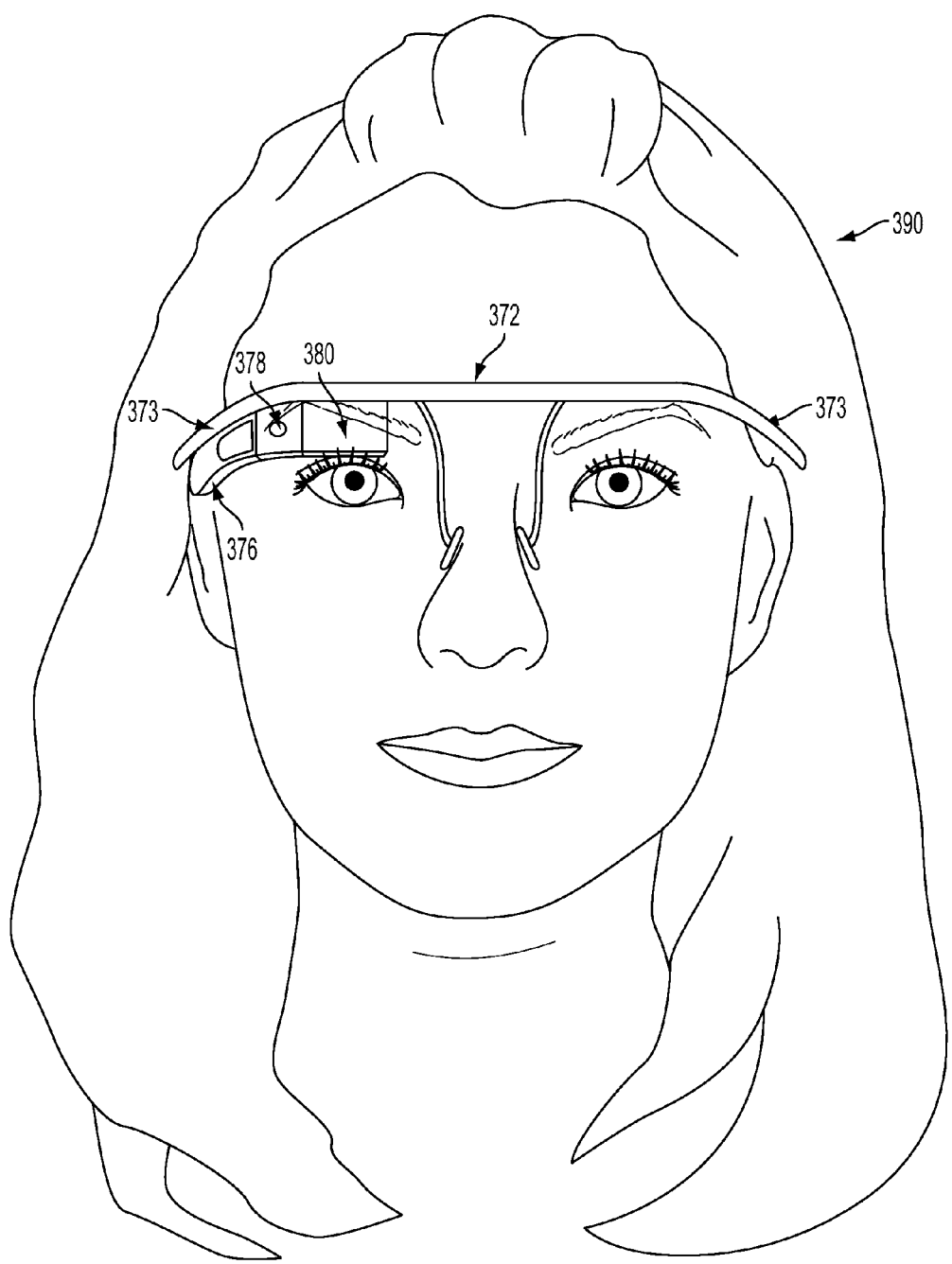
FIGS. 3B to 3D are simplified illustrations of the head-mountable device shown in FIG. 3A, being worn by a wearer.
Figure 3C:
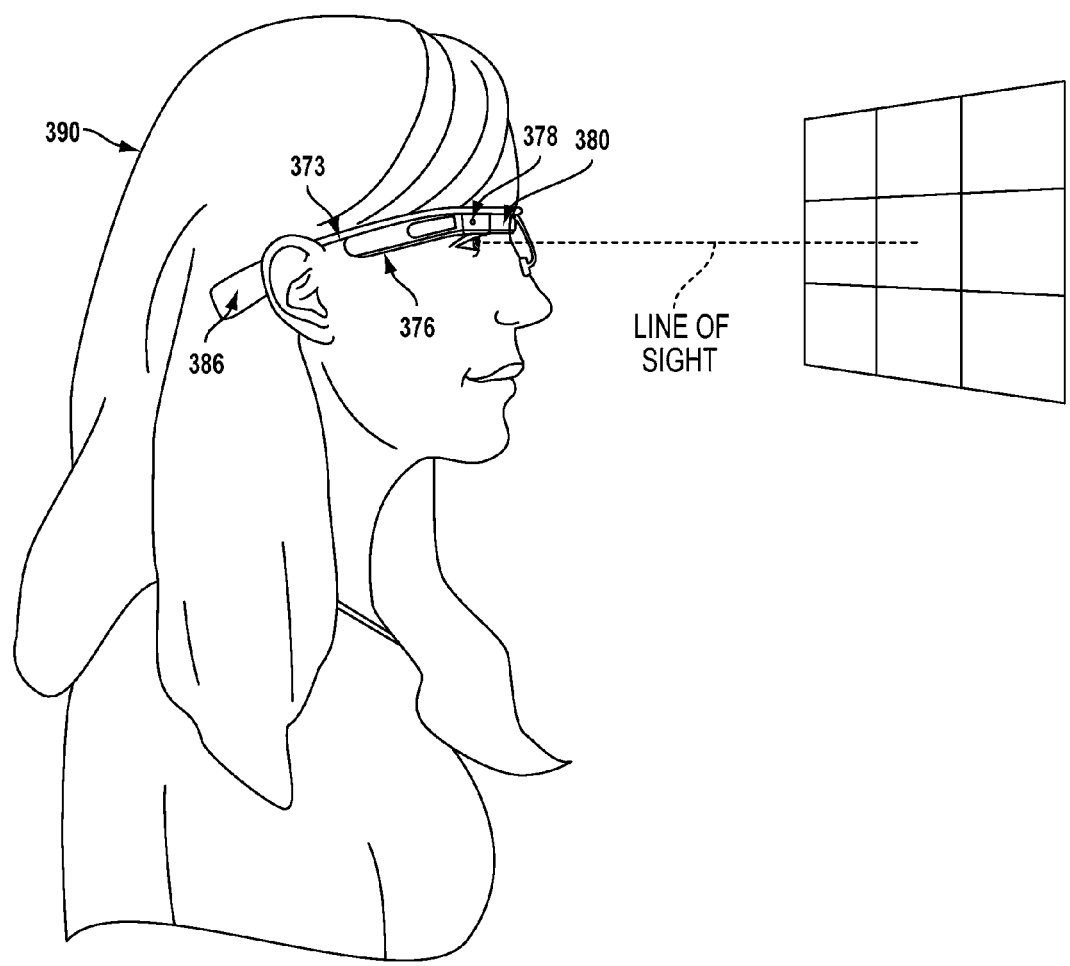
Figure 3D:
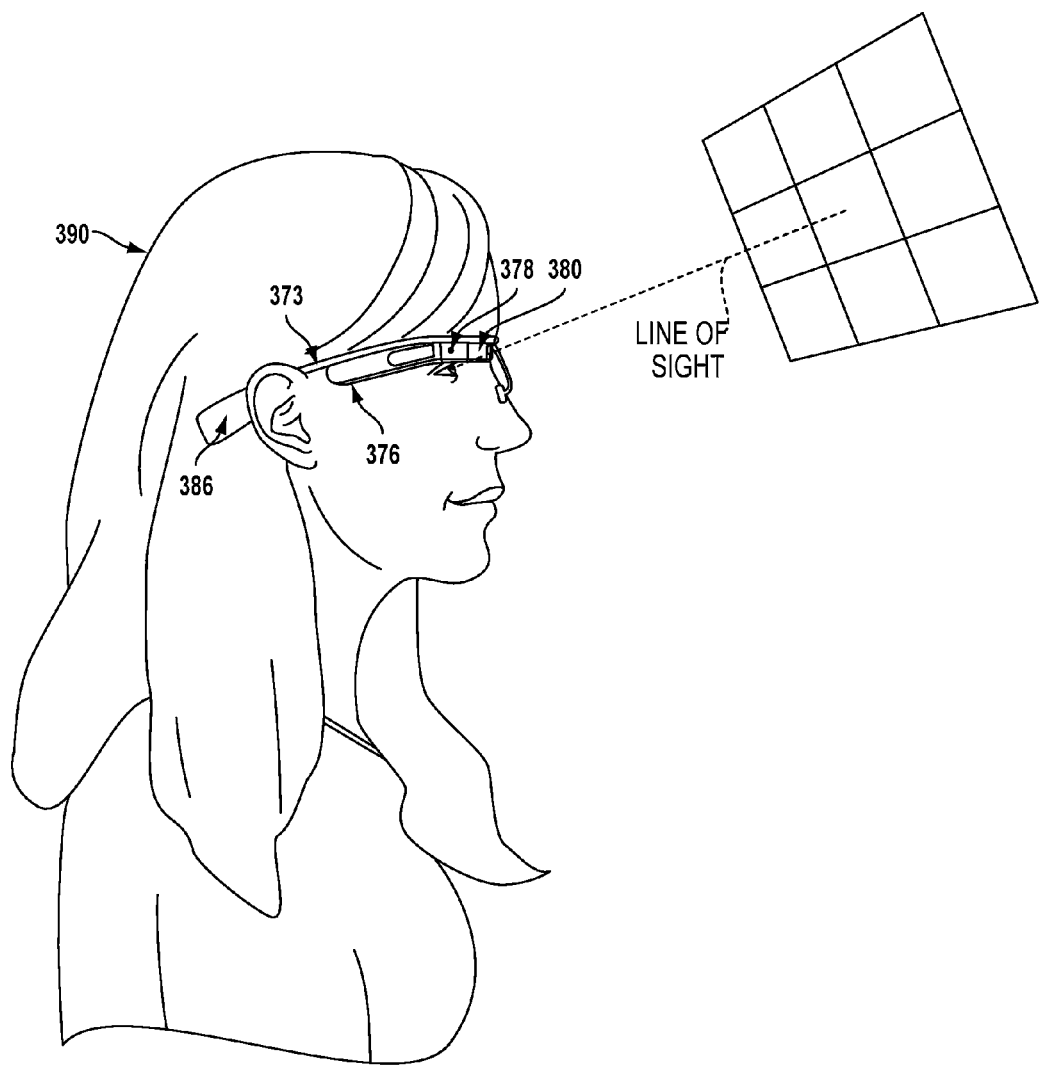

FIGS. 3B to 3D are simplified illustrations of HMD 372 shown in FIG. 3A, being worn by a wearer 390. In these examples, the optical system 380 can be arranged such that when HMD 372 is worn, optical system 380 is positioned in front of or proximate to a user's eye when HMD 372 is worn by a user. For example, optical system 380 can be positioned below the center frame support and above the center of the wearer's eye, as shown in FIG. 3B. Further, in the illustrated configuration, optical system 380 can be offset from the center of the wearer's eye (e.g., so that the center of optical system 380 is positioned to the right and above of the center of the wearer's eye, from the wearer's perspective).

Configured as shown in FIGS. 3B to 3D, optical system 380 can be located in the periphery of the field of view of the wearer 390, when HMD 372 is worn. Thus, as shown by FIG. 3C, when the wearer 390 looks forward, the wearer 390 can see the optical system 380 with their peripheral vision. As a result, optical system 380 can be outside the central portion of the wearer's field of view when their eye is facing forward, as it commonly is for many day-to-day activities. Such positioning can facilitate unobstructed eye-to-eye conversations with others, as well as generally providing unobstructed viewing and perception of the world within the central portion of the wearer's field of view. Further, when the optical system 380 is located as shown, the wearer 390 can view images emitted from the optical system 380 by, e.g., looking up with their eyes only (possibly without moving their head). When viewing images from the optical system 380, the retina of the user can be fluorescently imaged by the optical system 380. This is illustrated as shown in FIG. 3D, where the wearer has moved their eyes to look up and align their line of sight with optical system 380. A wearer might also use the optical system 380 by tilting their head down and aligning their eye with the optical system 380.

FIG. 4 is a functional block diagram of an HMD 400 that is configured to image a retina of a wearer of the device, according to an example embodiment. HMD 400 can be any type of device that can be mounted to the head of the wearer and image the retina of the wearer. For example, HMD 400 can be any one of the HMDs described with reference to FIGS. 1 to 3.

HMD 400 can include a head-mountable support 410, a light source 420, an imager 430, a processor 440, a system bus 450, and data storage 460. The head-mountable support 410 can be any structure that can be mounted to the head of the wearer and support the other components of the HMD 400 (e.g., 420, 430, 440, 450, 460) in an orientation in which the HMD 400 is able to image the retina of the wearer. The system bus 450 can be configured to facilitate communication between other components of the HMD 400 (e.g., between the processor 440 and the data storage 460) and/or to facilitate operation of components of the HMD 400 by the processor 440 (e.g., the light source 420 and/or the imager 430).

The light source 420 can be any light source capable of producing light of a wavelength corresponding to an excitation wavelength of a fluorophore. The light source could include an LED, a laser, or some other type of light-producing element. The light source 420 could additionally include optics that could include elements configured to direct the light produced by the light source 420 toward the retina of the wearer. The optics could additionally or alternately include elements to filter the light produced by the light source 420 such that only a narrow band of wavelengths corresponding to the excitation wavelength of the fluorophore are directed toward the retina of the wearer.

The imager 430 can be any element capable of detecting light emitted by a fluorophore in the retina of the user and generating an image of the emitted light. The imager 430 could include an array of photodetectors. In one example, the array of photodetectors could include CMOS active pixel elements. In another example, the imager could include a CCD image sensor array. The imager could be configured to be sensitive to light of a wavelength corresponding to an emission wavelength of the fluorophore. For example, the imager could include a filter that selectively passes light of wavelengths corresponding to the emission wavelength. The imager could alternatively or additionally be configured to be insensitive to light of a wavelength corresponding to the wavelength of the light emitted by the light source 420. The imager 430 could include optics to ensure that light from the retina of the wearer is imaged in-focus by the light-sensitive elements of the imager 430.

The processor 440 is in communication with data storage 460. Data storage 460 is a non-transitory computer-readable medium that can include, without limitation, magnetic disks, optical disks, organic memory, and/or any other volatile (e.g. RAM) or non-volatile (e.g. ROM) storage system readable by the processor 440. Data storage 460 can include program instructions 470 that can be executed by the processor 440 to cause the HMD 400 to perform functions specified by the program instructions 470. For example, the program instructions 470 can cause the HMD 400 to perform any of the functions described herein. Data storage 460 can also include other information. For example, data storage 460 could contain parameter and configuration data necessary for the operation of the HMD 400 or for performance of the functions specified by the program instructions 470. In another example, data storage 460 could be used by the processor 440 to store data relating to the operation of the HMD 400. For example, data storage 460 could be used to store images of the retina of the wearer that could be generated by the imager 430 or could be used to store a record of the timing of use of the HMD 400 by the wearer.

Program instructions 470 could include instructions which could be executed by the processor to operate the light source 472. Operating the light source 472 could include powering the light source 420 to produce light of a wavelength corresponding to an excitation wavelength of the fluorophore. Operating the light source 472 could further include controlling to level of light produced by the light source 420 according to an application; for example, controlling the level of light produced by the light source 420 such that it is at the lowest level necessary to image the retina, in order to minimize power usage by the HMD 400. Operating the light source 472 could include producing light from the light source 420 once or a plurality of times. The timing of producing light form the light source 420 could be periodic or could be variable according to an application.

Program instructions 470 could include instructions which could be executed by the processor to operate the imager 474. Operating the imager 474 could include powering the imager 430, configuring the imager 430 to generate an image or images, initiating generation of an image or images by the imager 430, and receiving data from the imager 430 corresponding to an image or images generated by the imager 430. Operating the imager 474 could include initiating generation of an image by the imager 430 during a time period when the light source 420 is producing light. Operating the imager 474 could also include initiating generation of an image by the imager 430 during a time period when the light source 420 was not producing light. Operating the imager 474 could include initiating generation of images by the imager 430 at a plurality of points in time, according to an application.

Program instructions 470 could include instructions which could be executed by the processor to determine one or more features of a retina based on one or more images of the retina 476. In an example, determining one or more features of a retina based on one or more images of the retina 476 could include determining a pattern of retinal vasculature from an image of the retina. For example, if a fluorophore was diffusely located in the vasculature of the retina, a fluorescent image of the retina generated by the imager 430 could indicate the location of the vasculature (for example, as described below for FIG. 5B). The location of the vasculature could be processed into a pattern of retinal vasculature.

In another example, determining one or more features of a retina based on one or more images of the retina 476 could include determining a gaze direction of the retina. For example, a pattern of retinal vasculature could be determined as described above. From this pattern, a location of an optic disc of the wearer could be determined. A gaze direction could be determined based on the determined location of the optic disc and information on the relationship between the optic disc and the gaze direction for the wearer that could be stored in data storage 460.

Other methods of determining a gaze direction could be included in determining one or more features of a retina based on one or more images of the retina 476. In one example, a fluorophore could be diffusely localized in the optic disc of the wearer. A fluorescent image of the retina generated by the imager 430 could indicate a location of the optic disc (for example, as described below for FIG. 5C). A gaze direction could be determined based on the determined location of the optic disc and information on the relationship between the optic disc and the gaze direction for the wearer that could be stored in data storage 460.

In another example, determining one or more features of a retina based on one or more images of the retina 476 could include determining the presence and/or concentration of a medically-relevant analyte in a retina. In an example, the medically-relevant analyte could be an amyloid plaque, and a fluorescent nanoparticle that selectively binds to the amyloid plaque (e.g., curcumin) could be introduced into the vasculature of the wearer. The nanoparticle could bind to the medically-relevant analyte and could be present in the retina at discrete points such that the image produced by the imager 430 could include a set of discrete points corresponding to the location of the nanoparticle bound to the medically-relevant analyte (for example, as described below for FIG. 5D). The presence and/or concentration of the medically relevant analyte could be determined from the number and/or intensity of the imaged points corresponding to the location of the nanoparticle bound to the medically-relevant analyte. In another example, the nanoparticle bound to the medically-relevant analyte could be present in the retina diffusely such that the image produced by the imager 430 could include a pattern of emitted fluorescent light intensity corresponding to concentration of the nanoparticle bound to the medically-relevant at locations on the retina corresponding to locations in the imaged pattern (for example, as described below for FIG. 5B). The concentration of the medically-relevant analyte could be determined by summing the intensity of the emitted fluorescent light pattern across the image. Determining one or more features of a retina based on one or more images of the retina 476 could include determining the features described above using other methods. Determining one or more features of a retina based on one or more images of the retina 476 could include determining features other than those described here.

In another example, determining one or more features of a retina based on one or more images of the retina 476 could include determining a flow speed of blood in a vasculature of a retina. In an example, a fluorophore could be present in the vasculature of the wearer. The fluorophore could be present in the retina at discrete points such that the image produced by the imager 430 could include a set of discrete points corresponding to the location of the fluorophore in the retina (for example, as described below for FIG. 6A). The discrete fluorophores could be tracked across a number of fluorescent images of the retina taken at a number of points in time. A flow speed of blood in the vasculature of the retina could be determined by using the fluorescent images of the retina taken at a number of points in time to compare the distance traveled by the discrete fluorophore in different images to the time between the points in time at which the different images were taken.

In another example, determining one or more features of a retina based on one or more images of the retina 476 could include determining that a gaze direction of the eye of the wearer has changed and/or determining the direction, angle, and/or other properties of a change in the gaze direction of the eye of the wearer. In an example, a fluorophore could be present in the vasculature of the wearer. The fluorophore could be present in the retina at discrete points such that the image produced by the imager 430 could include a set of discrete points corresponding to the location of the fluorophore in the retina (for example, as described below for FIG. 6B). The discrete fluorophores could be tracked across a number of fluorescent images of the retina taken at a number of points in time. Using pattern matching, low- and/or high-pass filtering, optic flow analysis, and/or other techniques familiar to one skilled in the art, it could be possible to determine the direction, angle, and/or other properties of the change in gaze direction of the eye using the images before and after the change in gaze direction of the eye. Further, images of the eye could be taken at more than two points in time, and the images could be used to detect a change in the gaze direction of the eye and the determine properties of the change in the gaze direction of the eye.

Determining one or more features of a retina based on one or more images of the retina 476 could include determining other features of the retina than those disclosed here. Determining one or more features of a retina based on one or more images of the retina 476 could include determining multiple features of the retina. The features of the retina could be determined using the methods disclosed herein or other methods familiar to one skilled in the art.

The HMD 400 could include components in addition to those described here. For example, the HMD 400 could include a display, a user interface, a communications interface, a battery, a bone conduction transducer (BCT) or other components according to an application. Further, the program instructions 470 could include additional instructions that, when executed by the processor 430, could enable the HMD 400 to operate the additional components or could enable other functions in addition to those described here.

In some examples, the HMD 400 could image the retina of the wearer and store the image, without necessarily determining a feature of the retina. Alternatively, the stored image could be analyzed at a later time to determine one or more features of the retina. In some examples, the HMD 400 could image the retina of the wearer and communicate the image to another device or system. The HMD 400 could include a communication interface configured to enable communication with a server; fluorescent images of the retina generated by the HMD 400 could be communicated to the server using the communication interface. The server could then determine a feature of the retina, using the sent images, and send information to the HMD based on the determined features.

Example head mounted devices (HMDs) described above have been described as fluorescently imaging a single fluorophore in a retina by emitting light of a wavelength corresponding to an excitation wavelength of the fluorophore and detecting light emitted by the fluorophore using sensors which are sensitive to light of a wavelength corresponding to an emission wavelength of the fluorophore. However, HMDs which fluorescently image multiple fluorophores in a retina are anticipated. For example, an HMD could include a plurality of light sources each configured to produce light of a wavelength corresponding to an excitation wavelength of a fluorophore selected from a plurality of fluorophores. Additionally or alternatively, an HMD could include a plurality of sensors each sensitive to light of a wavelength corresponding to an emission wavelength of a fluorophore selected from the plurality of fluorophores. In another example, an HMD could include a light source configured to produce light of an adjustable wavelength, where the wavelength of the produced light can be adjusted to correspond to an excitation wavelength of a fluorophore selected from a plurality of fluorophores.

III. Example Fluorescent Images of a Retina

FIGS. 5A-5D and FIGS. 6A-6B illustrate example retinal images that could be generated using the devices or methods described herein. It is to be understood that these example images are intended to illustrate example operations of devices and methods described herein and are not intended to be limiting. Thus, other types of retinal images could be obtained and/or other types of operations or functions could be performed based on retinal images that are obtained.

Further, it is to be understood that the example images of FIGS. 5A-5D and 6A-6B are composed to reflect the character of images that are expected to be generated from the operation of the systems and methods described herein. That is, these example images are not generated from actual experimental data.

Figure 5A:
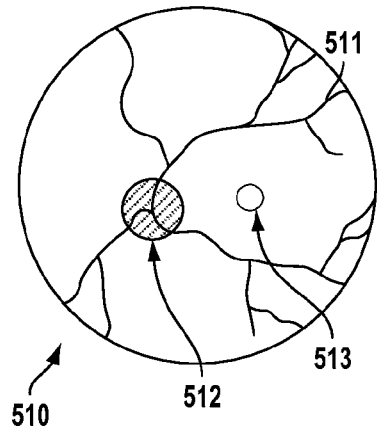
FIG. 5A illustrates an example retina of a wearer of a head-mountable device.

FIG. 5A illustrates an example visible-light image of a retina 510. This example visible-light image shows various structures in the retina 510, including retinal vasculature 511, an optic disc 512, and a macula 513. When the retina 510 is instead imaged using fluorescent light emitted by a fluorophore present in the retina 510 in response to illuminating the retina 510 with incident light at an excitation wavelength of the fluorophore, some of the structures in retina 510 may be more or less apparent.

Figure 5B:
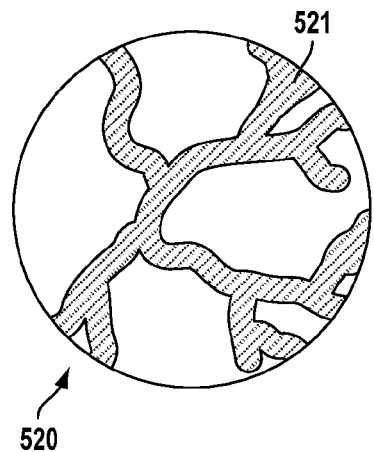
FIGS. 5B-5D are example images of the retina that could be generated by the head-mountable device

FIG. 5B illustrates an example fluorescent image of a retina 520 in which the fluorophore is diffusely located within the vasculature 521 of the retina 520. As a result, the pattern of the vasculature 521 corresponding to the fluorescent light emitted from the fluorophore is apparent in the image of FIG. 5B. The intensity of the fluorescent light could be related to the concentration of the fluorophore in the corresponding portion of the vasculature, the thickness (and thus volume) of the corresponding portion of the vasculature, and/or some other feature or features of the corresponding portion of the vasculature.

Figure 5C:
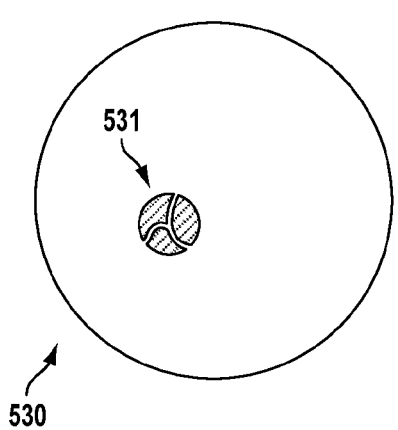

The fluorophore in the retina of the wearer of the HMD could be diffusely localized within or near some other aspect of the retina. For example, the fluorophore could be localized in or near the optic disc of the retina. FIG. 5C illustrates an example fluorescent image of a retina 530 in which a portion of the optic disc 531 is clearly visible, corresponding to the fluorescent light emitted from the fluorophore, and a portion of the optic disc 531 is not as visible because it is occluded by vasculature in the retina 530. The intensity of the light corresponding to a portion of the image could correspond to the amount of the fluorophore contained in the corresponding portion of the optic disc of the retina. The intensity of the light could be related to the concentration of the fluorophore in the corresponding portion of the optic disc, the presence of an occluding section of the retinal vasculature between the corresponding portion of the optic disc and an imaging device in the HMD, and/or some other feature or features of the corresponding portion of the optic disc. In other examples, the fluorophore could be diffusely localized in a macula of the retina, a diseased or damaged region of the retina (e.g., a region undergoing retinopathy), or some other feature or features of the retina.

Figure 5D:
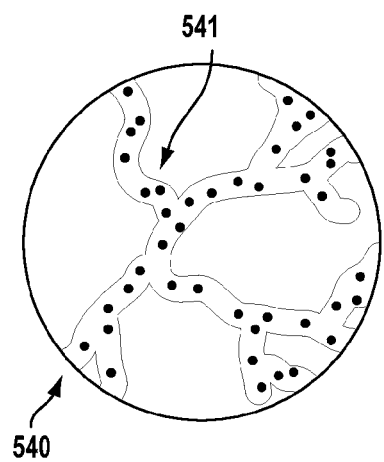

The fluorophore in the retina of the wearer could be localized within or near a set of discrete locations in the retina. For example, there could be a discrete number of fluorophores, or a discrete number of aggregates of fluorophores, in the vasculature of the retina. FIG. 5D includes an example fluorescent image of the retina of the wearer of the HMD 540 where the fluorophore being fluorescently imaged is located at or near a set of discrete points within the vasculature of the retina. As a result, the image could show a pattern of spots 541 corresponding to the fluorescent light emitted from the discrete fluorophores or the discrete aggregates of fluorophores. If the spots correspond to fluorophore aggregates, the intensity of the light corresponding to a spot in the image could correspond to the amount of the fluorophore contained in the corresponding fluorophore aggregate in the retina. There could be many discrete fluorophores or fluorophore aggregates in the image (as illustrated in FIG. 5D) or very few. If there are sufficiently many spots in the pattern of spots 541 it may be possible to determine a pattern of the vasculature of the retina. In other examples, the discrete fluorophores or fluorophore aggregates may not be contained in the vasculature of the retina, or they may be partially contained within the vasculature of the retina. For example, the optic disc, macula, or other features of the retina may contain discrete fluorophores or fluorophore aggregates.

Figure 6A:
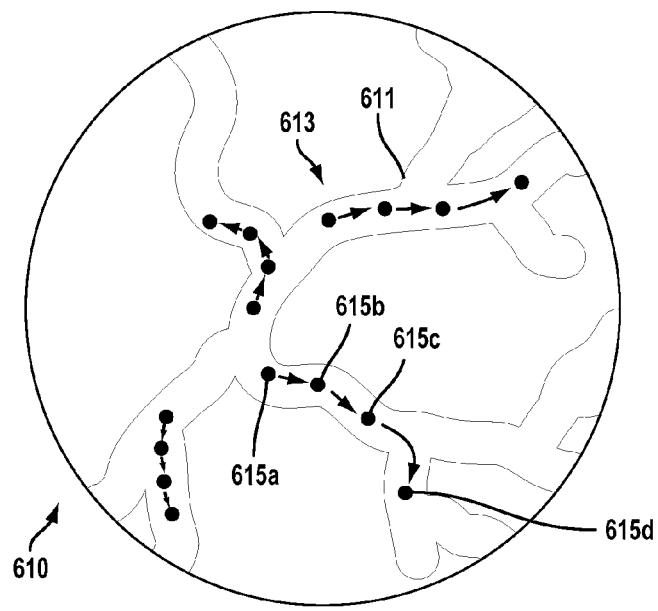
FIGS. 6A and 6B are example images of a retina of a wearer of a head-mountable device that could be generated by the head-mountable device.
Figure 6B:
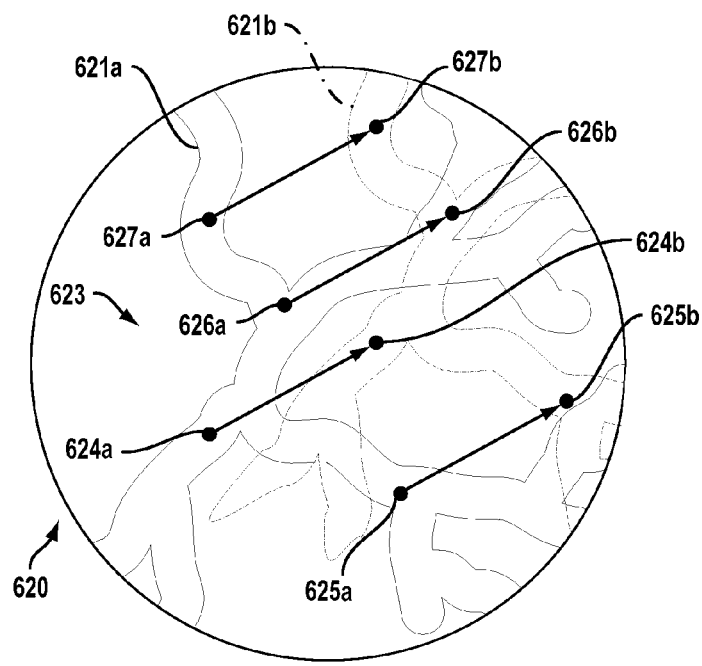

A retina of the wearer could be fluorescently imaged more than once. Further, features of the retina may be determined from the combination of multiple fluorescent images of the retina over time. FIGS. 6A and 6B illustrate example scenarios where the retina of the wearer contains a fluorophore contained within the vasculature of the retina. Further, the fluorophore is imaged as spots corresponding to discrete fluorophores or fluorophore aggregates (similar to the scenario described for FIG. 5D).

FIG. 6A includes several overlaid fluorescent images of the retina 610 where the fluorophore being fluorescently imaged is located at or near a set of discrete points within the vasculature of the retina. Further, the several fluorescent images are taken at several different points in time and the location and gaze direction of the eye relative to an imaging device in the HMD that generated the several fluorescent images do not substantially change across the several different points in time. A pattern of the retinal vasculature 611 is shown in grey for illustrative purposes. As a result, the images could show a pattern of spots 613 corresponding to the fluorescent light emitted from the discrete fluorophores or the discrete aggregates of fluorophores at the several different points in time.

Movement of individual fluorophores or fluorophore aggregates could also be detected. For example, an example discrete fluorophore may be imaged at four subsequent different points in time. An example spot 615a could be from an image taken at a first point in time and could correspond to the fluorescent light emitted by the example discrete fluorophore during the first point in time. Example spots 615b, 615c, and 615d could be from images taken at a second, a third, and a fourth point in time, respectively, and could correspond to the fluorescent light emitted by the example discrete fluorophore at the second, the third, and the fourth point in time, respectively. As blood flows through the vasculature of the retina, the discrete fluorophore could move with the blood through the vasculature. This could result in a series of spots (e.g., 615a-d) in a series of fluorescent images of the retina. The spots could correspond to the moving discrete fluorophore. The movement of the discrete fluorophore over time could be determined from the corresponding spots in the series of images. A speed of flow of the blood in the vasculature could be determined from the spots in the series of images. Analysis of patterns of flow of the blood over time could allow for the determination of other features of the retina of the wearer of the HMD; for example, a pulse rate could be determined. Analysis of a plurality of spots over a plurality of images taken at a plurality of points in time could allow the determination of the pattern of the vasculature.

FIG. 6B includes two overlaid fluorescent images of a retina 620 in which the fluorophore being fluorescently imaged is located at or near a set of discrete points within the vasculature of the retina. Further, the two fluorescent images are taken at two different points in time and the two different points in time correspond to a point in time before a change in a gaze direction of the eye and a point in time and after a change in the gaze direction of the eye, respectively. For illustrative purposes, a pattern of the retina of the wearer before the change 621a is shown in grey and a pattern of the retina of the wearer after the change 621b is shown in dashed grey. As a result, the two images could show a pattern of spots 623 corresponding to the fluorescent light emitted from the discrete fluorophores or the discrete aggregates of fluorophores before and after the change in the gaze direction of the eye. It may be possible to track the movement of individual fluorophores or fluorophore aggregates. For example, example discrete fluorophores may be imaged at two points in time corresponding to points in time before and after the change in the gaze direction of the eye. Example spots 624a, 625a, 626a, and 627a could be from an image taken at a first point in time before the change in the gaze direction of the eye and could correspond to the fluorescent light emitted by a first, a second, a third, and a fourth example discrete fluorophore, respectively, during the first point in time. Example spots 624b, 625b, 626b, and 627b could be from an image taken at a second point in time after the change in the gaze direction of the eye and could correspond to the fluorescent light emitted by the first, the second, the third, and the fourth example discrete fluorophore, respectively, at the second point in time. By using pattern matching, low- and/or high-pass filtering, optic flow analysis, and/or other techniques familiar to one skilled in the art, it could be possible to determine the direction, angle, and/or other properties of the change in the gaze direction of the eye using the images before and after the change in the gaze direction of the eye. Further, images of the eye could be taken at more than two points in time, and the images could be used to detect a change in the gaze direction of the eye and the determine properties of the change in the gaze direction of the eye.

IV. Example Methods

Figure 7:
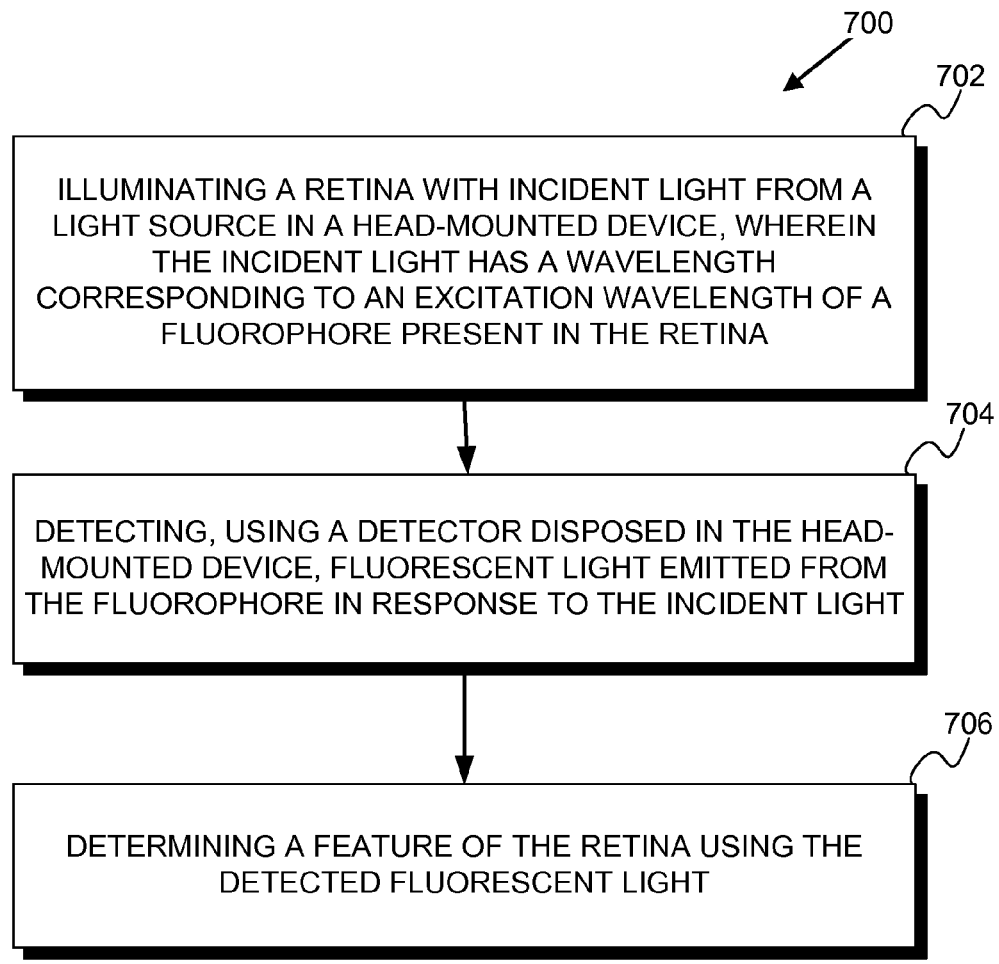
FIG. 7 is a flow chart of a method, according to an example embodiment.

FIG. 7 is a flowchart of a method 700 for imaging a retina of a wearer of a head-mounted device, using the head-mounted device. The method 700 includes illuminating the retina with incident light from a light source in the head-mounted device (HMD), wherein the incident light has a wavelength corresponding to an excitation wavelength of a fluorophore present in the retina (702). Illuminating the retina (702) could include powering the light source in the HMD. Illuminating the retina (702) could further include controlling the level of light produced by the light source in the HMD according to an application; for example, controlling the level of light produced by the light source in the HMD such that it is at the lowest level necessary to image the retina, in order to minimize power usage by the HMD. Illuminating the retina (702) could include producing light from the light source in the HMD once or a plurality of times. The timing of producing light form the light source in the HMD could be periodic or could be variable according to an application.

The method 700 also includes detecting, using a detector disposed in the head-mounted device (HMD), fluorescent light emitted from the fluorophore in response to the incident light (704). Detecting fluorescent light (704) could include powering the detector disposed in the HMD, configuring the detector disposed in the HMD to generate an image or images, initiating generation of an image or images by the detector disposed in the HMD, and receiving data from the detector disposed in the HMD corresponding to an image or images generated by the detector disposed in the HMD. Detecting fluorescent light (704) could include initiating generation of an image by the detector disposed in the HMD during a time period when the light source in the HMD is producing light. Detecting fluorescent light (704) could also include initiating generation of an image by the detector disposed in the HMD during a time period when the light source in the HMD was not producing light. Detecting fluorescent light (704) could include initiating generation of images by the detector disposed in the HMD at a plurality of points in time, according to an application.

The method 700 also includes determining a feature of the retina using the detected fluorescent light (706). Determining a feature of the retina (706) could include determining a pattern of retinal vasculature from an image of the retina generated by detecting fluorescent light (704). For example, if a fluorophore was diffusely located in the vasculature of the retina, a fluorescent image of the retina generated by the detector disposed in the HMD could indicate the location of the vasculature (for example, as described above for FIG. 5B). The location of the vasculature could be processed into a pattern of retinal vasculature. Determining a feature of the retina (706) could additionally or alternatively include determining a diameter or diameters of the vasculature of the retina. A disease or deformation of the retina or of the vasculature of the retina could be diagnosed based at least on the determined pattern and/or diameters of the vasculature of the retina.

In another example, determining a feature of the retina (706) could include determining a gaze direction of the retina. For example, a pattern of retinal vasculature could be determined as described above. From this pattern, a location of an optic disc of the wearer could be determined. A gaze direction could be determined based on the determined location of the optic disc and information on the relationship between the optic disc and the gaze direction for the wearer.

Other methods of determining a gaze direction could be included in determining a feature of the retina (706). In one example, a fluorophore could be diffusely localized in the optic disc of the wearer. A fluorescent image of the retina generated by the detector disposed in the HMD could indicate a location of the optic disc (similar to the scenario described for FIG. 5C). A gaze direction could be determined based on the determined location of the optic disc and information on the relationship between the optic disc and the gaze direction for the wearer.

The method 700 could further include operating the HMD based on the determined gaze direction. For example, the HMD could use the gaze direction to determine an object in the environment of the wearer that is the target of the wearer's gaze. In another example, the HMD could present a virtual image to the wearer of the HMD. The gaze direction could be used to determine an object in the virtual image that the wearer was looking at and the operation of the HMD could be altered based on the identity of the determined object. For example, the HMD could perform a function associated with the determined object. In another example, the HMD could alter the virtual image based the identity of the determined object. For example, the HMD could shift the virtual image so that the determined object was moved toward the center of a field of view of the virtual image. In another example, the determined object could increase or decrease in size. Other methods of operating the HMD based on the determined gaze direction are possible.

In another example, determining a feature of the retina (706) could include determining the presence and/or concentration of a medically-relevant analyte in the retina. In an example, the medically-relevant analyte could be an amyloid plaque, and a fluorescent nanoparticle that selectively binds to the amyloid plaque (e.g., curcumin) could be introduced into the vasculature of the wearer. The nanoparticle bound to the medically-relevant analyte could be present in the retina at discrete points such that the image produced by the detector disposed in the HMD could include a set of discrete points corresponding to the location of the nanoparticle bound to the medically-relevant analyte (similar to the scenario described for FIG. 5D). The presence and/or concentration of the medically relevant analyte could be determined from the number and/or intensity of the imaged points corresponding to the location of the nanoparticle bound to the medically-relevant analyte. In another example, the nanoparticle bound to the medically-relevant analyte could be present in the retina diffusely such that the image produced by the detector disposed in the HMD could include a pattern of emitted fluorescent light intensity corresponding to concentration of the nanoparticle bound to the medically-relevant at locations on the retina corresponding to locations in the imaged pattern (for example, as described above for FIG. 5B). The concentration of the medically-relevant analyte could be determined by summing the intensity of the emitted fluorescent light pattern across the image. Determining a feature of the retina (706) could include determining the features described above using other methods. Determining a feature of the retina (706) could include determining features other than those described here.

In another example, determining a feature of the retina (706) could include determining a flow speed of blood in a vasculature of a retina. In an example, a fluorophore could be present in the vasculature of the wearer. The fluorophore could be present in the retina at discrete points such that the image produced by the detector disposed in the HMD could include a set of discrete points corresponding to the location of the fluorophore in the retina (for example, described above for FIG. 6A). The discrete fluorophores could be tracked across a number of fluorescent images of the retina taken at a number of points in time. A flow speed of blood in the vasculature of the retina could be determined by using the fluorescent images of the retina taken at a number of points in time to compare the distance traveled by the discrete fluorophore in different images to the time between the points in time at which the different images were taken.

In another example, determining a feature of the retina (706) could include determining that a gaze direction of the eye of the wearer has changed and/or determining the direction, angle, and/or other properties of a change in the gaze direction of the eye of the wearer. In an example, a fluorophore could be present in the vasculature of the wearer. The fluorophore could be present in the retina at discrete points such that the image produced by the detector disposed in the HMD could include a set of discrete points corresponding to the location of the fluorophore in the retina (for example, as described above for FIG. 6B). The discrete fluorophores could be tracked across a number of fluorescent images of the retina taken at a number of points in time. Using pattern matching, low- and/or high-pass filtering, optic flow analysis, or other techniques familiar to one skilled in the art, it could be possible to determine the direction, angle, and/or other properties of the change in the gaze direction of the eye using the images before and after the change in the gaze direction of the eye. Further, images of the eye could be taken at more than two points in time, and the images could be used to detect a change in the gaze direction of the eye and the determine properties of the change in the gaze direction of the eye.

Determining a feature of the retina (706) could include determining other features of the retina than those disclosed here. Determining a feature of the retina (706) could include determining multiple features of the retina. The features of the retina could be determined using the methods disclosed herein or other methods familiar to one skilled in the art.

The method 700 could include further steps. In some examples, determining a feature of the retina (706) could include determining a pattern of retinal vasculature. In some examples, method 700 could further include comparing the determined pattern of the retinal vasculature to a stored pattern. For example, a pattern of retinal vasculature of a wearer of an HMD could be determined and compared to a stored pattern. If the comparison finds that the determined pattern of the wearer is similar enough to the stored pattern, the operation of the HMD could be altered according to information associated with the stored pattern. For example, functions specified by the information associated with the stored pattern could be enabled. In another example, the HMD could identify the wearer of the HMD to other systems in communication with the HMD based on the information associated with the stored pattern. Other functions could be performed based on the comparison of a determined pattern of the retinal vasculature of the wearer of the HMD to a stored pattern. In other examples, method 700 could further include detecting a disease or deformation of the retina using the determined pattern of the retinal vasculature. For example, the determined pattern of the retinal vasculature could be used to determine whether a wearer of the HMD was experiencing hypertensive retinopathy, diabetic retinopathy, one or more retinal macroaneurisms, or some other disorder of the retina or retinal vasculature.

CONCLUSION

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

Further, where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

In situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from a content server that may be more relevant to the user. In addition, certain data may be treated in one or more ways before it is stored or used, so that personally identifiable information is removed. For example, a user's identity may be treated so that no personally identifiable information can be determined for the user. Thus, the user may have control over how information is collected about the user and used by a content server.

We claim:

1. A device comprising:
   a head-mountable support;
   a light source supported by the head-mountable support, wherein the light source is positioned to illuminate a retina in an eye of a wearer of the device with incident light, wherein the incident light has a wavelength corresponding to an excitation wavelength of fluorescent nanoparticles, wherein the fluorescent nanoparticles selectively bind to a target analyte; and
   an imager supported by the head-mountable support, wherein the imager is positioned to image the retina using fluorescent light emitted from the fluorescent nanoparticles in response to the incident light, and wherein the imager includes a filter that substantially blocks the wavelength of the incident light and passes the fluorescent light.

2. The device of claim 1, further comprising:
   a processor; and
   data storage, wherein the data storage contains instructions that can be executed by the processor to perform functions, wherein the functions comprise (i) operating the light source to illuminate the retina, (ii) operating the imager to produce one or more images of the retina, and (iii) determining a presence or concentration of the target analyte in the retina based on the one or more images of the retina.

3. The device of claim 1, further comprising:
   a display supported by the head-mountable support, wherein the display is configured to generate a light pattern.

4. The device of claim 3, further comprising:
   an optical system supported by the head-mountable support, wherein the optical system optically couples the display and the imager to the retina, such that the retina is at a focal plane that is conjugate to both a first focal plane at the display and a second focal plane at the imager.

5. The device of claim 3, wherein the display comprises:
   a display light source, and
   a light modulator, wherein the light modulator spatially modulates light from the display light source to generate the light pattern.

6. The device of claim 1, wherein the fluorescent nanoparticles each comprise a target-specific binding moiety.

7. The device of claim 1, wherein the fluorescent nanoparticles each comprise a nanoparticle functionalized with a fluorophore.

8. The device of claim 1, wherein the fluorescent nanoparticles each comprise curcumin.

9. The device of claim 1, wherein the fluorescent nanoparticles each comprise an antibody.

10. The device of claim 1, wherein the light source is positioned to illuminate the retina off-axis relative to the imager.

11. The device of claim 1, wherein the light source is positioned to illuminate the retina through a temple of the wearer.

* * * * *